United States Patent [19]

Yardley

[11] 4,133,805
[45] Jan. 9, 1979

[54] CYCLIC UNDECAPEPTIDES RELATED TO SOMATOSTATIN AND INTERMEDIATES THEREFOR

[75] Inventor: John P. Yardley, King of Prussia, Pa.

[73] Assignee: American Home Products Corporation, New York, N.Y.

[21] Appl. No.: 641,218

[22] Filed: Dec. 16, 1975

[51] Int. Cl.² .................. C07C 103/52; A61K 37/00
[52] U.S. Cl. ............................. 260/112.5 S; 424/177
[58] Field of Search ................. 260/112.5 S; 424/177

[56] References Cited

U.S. PATENT DOCUMENTS 3,904,594  9/1975  Guillenin et al. ............. 260/112.5 S Primary Examiner—Delbert R. Phillips Attorney, Agent, or Firm—Robert Wiser

[57] ABSTRACT

Cyclic undecapeptides of the general formula

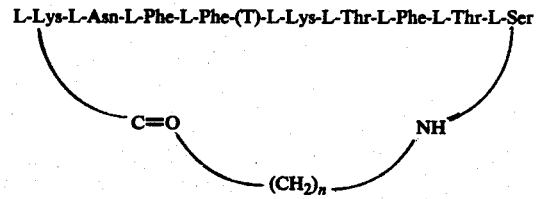

wherein n is an integer of from 3 to 8 and T may be either L-Trp or D-Trp are disclosed. These compounds inhibit the release of pituitary growth hormone, glucagon, and insulin.

7 Claims, No Drawings

CYCLIC UNDECAPEPTIDES RELATED TO SOMATOSTATIN AND INTERMEDIATES THEREFOR

BACKGROUND OF THE INVENTION

The cyclic somatotropin-release inhibiting factor (SRIF), known as somatostatin, has been shown [Brazeau et al., Science, 179, 77 (1973)] to have the following structure:

H-Ala-Gly-
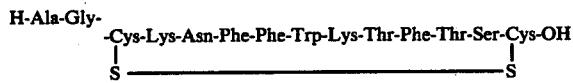

Several methods for synthesizing somatostatin have been reported in the literature including the solid phase method of Rivier, J. Am. Chem. Soc., 96, 2986 (1974), and the solution methods of Sarantakis et al., Biochemical Biophysical Research Communications, 54, 234 (1973), and Immer et al., Helv. Chim. Acta, 57, 730 (1974); and there is much on-going peptide research whose goal is to enhance somatostatin's pharmacological activity by synthetically modifying its structure.

The present invention provides novel cyclic analogs of somatostatin wherein its tryptophyl residue may be either of the L or D stereochemical configuration and wherein its ala$^1$, gly$^2$, cys$^3$ and cys$^{14}$ residues have been replaced by an ω-amino acid of the general formula $H_2N-(CH_2)_{3-8}-COOH$. Replacement of the L-Trp residue in somatostatin by D-Trp is discussed by J. Rivier et al., Biochem. Biophys. Res. Commun., 65, 746 (1975).

SUMMARY OF THE INVENTION

The invention sought to be patented resides in the concept of a compound selected from the class consisting of:

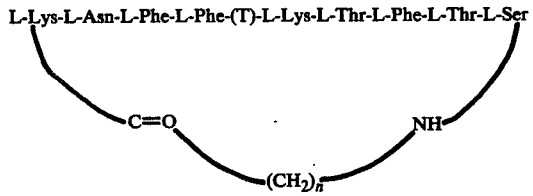

and

R$^1$NH(CH$_2$)$_n$CO—L—Lys(R$^2$)—L—Asn—L—Phe—L—Phe—(T)—L—Lys(R$^2$)—L—Thr(R$^3$)—L—Phe—L—Thr(R$^3$)—L—Ser(R$^3$)—X and its non-toxic salts; wherein R$^1$ is selected from the group consisting of hydrogen and t-butyloxycarbonyl; R$^2$ is 2-chlorobenzyloxycarbonyl; R$^3$ is benzyl; n is an integer of from 3 to 8; T is selected from the group consisting of L-Tryptophyl and D-Tryptophyl; and X is selected from the group consisting of OH, NH-NH$_2$, O-(lower)-alkyl, O-benzyl and an anchoring bond linked to a solid polystyrene resin represented by:

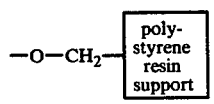

The cyclic embodiments of the invention possess the inherent physical properties of being white to light tan colored solids, are substantially insoluble in chloroform, benzene, and the like, but exhibit solubility in water and aqueous acid solutions such as hydrochloric and acetic. These compositions display no clearly discernable melting points and may be purified by, for example, chromatographic means. Hydrolysis of these compositions in, for example, 4N methanesulfonic acid allows determination of their amino acid content, which is consistent with the structures as hereinbefore set forth.

The cyclic embodiments of the invention possess the applied use characteristic of inhibiting the release of growth hormone insulin and glucagon as evidenced by standard pharmacological test procedures.

The invention sought to be patented in a second aspect resides in the concept of the cyclic undecapeptide of the formula:

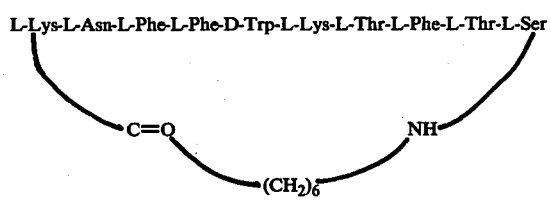

and the non-toxic salts thereof.

The invention sought to be patented in a third aspect resides in the concept of the cyclic undecapeptide of the formula:

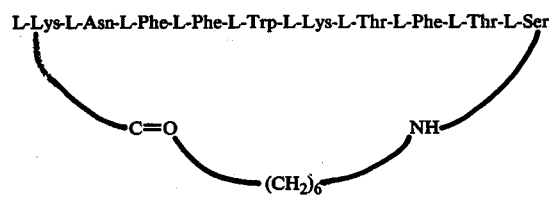

and the non-toxic salts thereof.

DESCRIPTION OF THE INVENTION

The cyclic undecapeptides of the present invention which inhibit the secretion of the hormone somatotropin are represented by the formula:

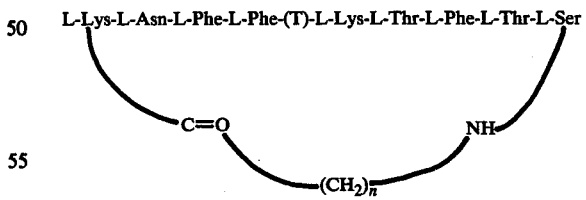

wherein T is chosen from L-tryptophyl and D-tryptophyl, n is an integer of from 3-8, and the non-toxic acid addition salts thereof. Illustrative of the non-toxic acids for preparing these salts are hydrochloric, acetic, sulfuric, maleic, benzoic, fumaric, citric and the like.

The present invention also relates to novel undecapeptide intermediates of the formula:

R$^1$NH(CH$_2$)$_n$CO—L—Lys(R$^2$)—L—Asn—L—Phe—L—Phe—(T)—L—Lys(R$^2$)—L—Thr(R$^3$)—L—Phe—L—Thr(R$^3$)—L—Ser(R$^3$)—X wherein n is an integer of from 3-8, T is chosen from D-tryptophyl and L-tryptopyl; $R^1$ is either hydrogen or an α-amino protecting group preferably of the urethane type such as t-butyloxycarbonyl; $R^2$ is halobenzyloxycarbonyl, benzyloxycarbonyl, etc. and is preferably 2-chlorobenzyloxycarbonyl; $R^3$ is benzyl; X is selected from the group consisting of OH, NH—NH$_2$, O-(lower)alkyl, O-benzyl, and an anchoring bond linked to a solid polystyrene resin represented by:

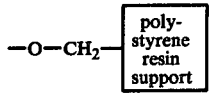

The polystyrene resin support may be any suitable resin conventionally employed in the art for solid phase preparation of polypeptides and is preferably a copolymer of styrene with about 1 to 2% divinyl benzene as a cross linking agent which causes the polystyrene polymer to be insoluble in certain organic solvents. It has also preferably been chloromethylated to provide sites for ester formation with the initially introduced amino protected amino acid. The polystyrene polymer is composed of long alkyl chains bearing a phenyl ring on every second carbon and the terminal amino acid residue is joined through a covalent carbon to oxygen bond to this resin support.

The linear sequences from which the cyclic undecapeptides of this invention are prepared are themselves preferably prepared by solid phase methodology, following techniques generally known in the art for building an amino acid sequence from an initial resin supported amino acid. Merrifield, J.A.C.S., 85, 2149 (1963), generally illustrates the technique involved. The linear sequences are then removed from the resin support and cyclized intramolecularly producing the novel cyclic undecapeptides of the invention.

Because of the cyclic nature of the product undecapeptides, it is immaterial which amino acid in the sequence is chosen to initiate the synthesis of the linear intermediate therefore; provided that this linear sequence is assembled in the order one would encounter by moving counter-clockwise around the undecapeptide cycle from the amino acid so chosen. For reasons of convenience, the undecapeptides of the instant invention have been assembled using L-serine as the starting amino acid, thus L-serine appears (reading right to left) as the first amino acid residue in the sequence of the linear intermediates. It thus follows that the ω-amino acid of formula H$_2$N(CH$_2$)$_{3-8}$—COOH will appear as the last amino acid residue in the sequence of the linear intermediates (again reading right to left). An amide bond produced by reacting the carboxyl group of the L-serine residue and the amino group of the ω-amino acid residue completes the synthesis. It will be obvious to those skilled in the art that if an amino acid other than L-serine is chosen for the starting point in the synthesis, the sequence of the linear intermediates will vary but, once cyclized, the required amino acid sequence will be presented by the product undecapeptide cycle. Thus, for example, the following amino acid sequence is required of the linear intermediate (reading right to left) to produce the cyclic undecapeptides of the invention if D-tryptophan is chosen to initiate the linear sequence:

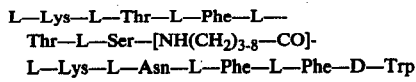

The formation, intramolecularly, of an amide bond between the carboxyl group of D-tryptophan and the α-amino group of the end chain lysine residues will produce the cyclic undecapeptides of the invention. A particular benefit which may be derived from employing an ω-amino alkanoic acid to initiate the linear sequence, i.e. the first amino acid attached to the resin, is freedom from racemization either on removal from the resin or on activation.

In a preferred sequence, the α-amino-β-hydroxy protected amino acid t-Boc-O-benzyl-L-serine is coupled at its carboxyl group to the chloromethylated resin according to the procedure of Gisin, Helv. Chim. Acta., 56, 1476 (1973). Following the coupling of α-amino-β-hydroxy di-protected L-serine to the resin support, the α-amino protecting group is removed by standard methods preferably employing trifluoroacetic acid in methylene chloride containing 5% ethanedithiol, or by means of trifluoroacetic acid alone of by means of HCl in dioxane. The deprotection is preferably carried out at a temperature between about 0° C. and room temperature. The remaining α-amino protected amino acids are coupled, seriatim, in the desired order to obtain the linear sequence which may be cyclized to the desired product. Alternatively, multiple amino acid groups may be coupled by the solution method prior to coupling with the resin supported amino acid sequence, to produce the desired linear intermediate. The selection of an appropriate coupling reagent is within the skill of the art. A particularly suitable coupling reagent is N,N'-diisopropyl carbodiimide (DIC). Another suitable coupling agent is N,N'-dicyclohexylcarbodiimide (DCC).

Each protected amino acid or amino acid sequence is introduced into the solid phase reactor in a two to six fold excess and the coupling is carried out in a medium of dimethyl-formamide:methylene chloride or in either dimethylformamide or methylene chloride alone. In cases where incomplete coupling occurs the coupling procedure is repeated before removal of the α-amino protecting group, prior to introduction of the next amino acid to the solid phase reactor. The success of the coupling reaction at each stage of the synthesis is monitored by the ninhydrin reaction as described by E. Kaiser et al., Analyt. Biochem., 34, 595 (1970).

The fully protected, resin supported undecapeptide presents the preferred amino acid sequence

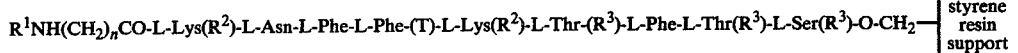

in which the group

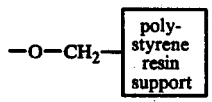

represents the ester moiety of one of the many functional groups present in the polystyrene resin, the $R^{1-3}$ groups, n, and T are as defined above.

The fully protected linear amino acid sequence is separated from the polystyrene resin support, the $R^1$ group is removed, and the linear peptide is subjected to intramolecular cyclization, the remaining blocking groups (i.e. $R^2$ and $R^3$) are removed, the cyclic deblocked undecapeptide is purified by, for example, chromatographic means, and if desired, the free cyclic undecapeptide is converted to a pharmacologically acceptable acid addition salt.

A particularly convenient and efficacious sequence for performing the above steps is described below. This outlined procedure discloses preferred methods, other procedures for performing the requisite reaction steps will be obvious to those skilled in the art, and are considered equivalents to those herein disclosed.

The fully protected linear amino acid sequence may be removed from the polystyrene resin support by treatment with 97% hydrazine, this treatment produces a linear undecapeptide of the following structure:

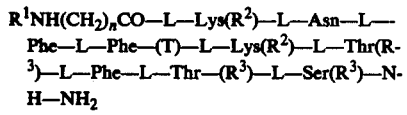

wherein $R^1$, $R^2$, $R^3$, n and T are as defined above. The $R^1$ group, when t-Boc, may next be removed by treatment with, for example, anhydrous trifluoroacetic acid after which the intramolecular cyclization is carried out. Alternately, the $R^1$, group, when t-Boc, may be removed from the resin supported linear sequence by treatment with, for example, anhydrous trifluoroacetic acid prior to the hydrazinolysis procedure. The free ω-amino undecapeptide hydrazide is treated with, for example, t-butylnitrite in acid medium at about −25° C. for about 30 minutes. At this time a negative reaction to Tollens Reagent indicates the absence of hydrazide. The mixture is next diluted to approximately 30–40x volume with a reaction inert solvent such as dimethylformamide at about −20° C., the pH is adjusted to ca. 8 with, for example, diisopropylethylamine and is allowed to remain at 0° C. for about 3 to about 5 days. The high dilution favors intramolecular cyclization. The solvent is next evaporated and the residue may be precipitated by, for example, addition to 1% acetic acid and allowing to stand at 0° C. overnight. The product is next completely deblocked (i.e. the $R^2$ and $R^3$ groups are removed) by treatment with, for example, anhydrous hydrogen fluoride and anisole at 0° C. for about 1 hour. After removal of the hydrogen fluoride, the residue may be purified by procedures familiar to those skilled in the art, for example trituration, followed by chromatography.

The in vivo pharmacological activity of the cyclic undecapeptides of the present invention was established by the following procedures. For purposes of convenience in reporting the test results, the compound cyclic(7-aminoheptanoyl-L-lysyl-L-asparaginyl-L-phenylalanyl-L-phenylalanyl-L-tryptophyl-L-lysyl-L-threonyl-L-phenylalanyl-L-threonyl-L-seryl) is referred to as compound A; and the compound cyclic(7-aminoheptanolyl-L-lysyl-L-asparaginyl-L-phenylalanyl-l-phenylalanyl-D-tryptophyl-L-lysyl-L-threonyl-L-phenylalanyl-L-threonyl-L-seryl) is referred to as compound B.

TEST PROCEDURE I

A subcutaneous (sc) injection of peptide solubilized or suspended in physiological saline, is given to Charles River CD ® nonfasted male rats. Matched saline control solution sc injected rats serve as control animals so that every experimental rat is paired with a control rat. The rats are kept in separate cages and 20 minutes before the end of the test time period they are given an intraperitoneal (i.p.) injection of Nembutal ® at a dose of 50 mg/kg. Blood samples are obtained by cardiac puncture and the plasma separated for the radioimmunoassay of growth hormone (GH) concentration (ng/ml). Time periods after injection of 1, 2, or 4 hours are generally used to test the duration of the activity of the peptide to surpress circulating peripheral GH levels. Comparisons between control and experimental GH values at each time are evaluated by the Student "t" test and statistical significance (p) at the 0.05 level or lower is used as the index of activity.

| Compound (Dose) | 1 Hr. (No. Rats) | 2 Hr. (No. Rats) | 4 Hr. (No. Rats) |
|---|---|---|---|
| A (1 mg/kg) | 95 ± 47 (7) | 80 ± 12 (9) | — |
| Control | 370 ± 103 (10) | 270 ± 90 (10) | — |
|  | p = 0.05 | p = 0.05 |  |
| B (2 mg/kg) | 13 ± 1.7 (10) | 15 ± 2.8 (10) | — |
| Control | 301 ± 73 (10) | 103 ± 31 (9) | — |
|  | p = <0.001 | p = <0.01 |  |
| B (1 mg/kg) | — | 44 ± 12 (8) | 46 ± 6 (10) |
| Control | — | 233 ± 42 (10) | 90 ± 15 (9) |
|  |  | p = <0.001 | p = 0.02 |
| B (0.25 mg/kg) | — | 108 ± 18 (9) | 84 ± 17 (9) |
| Control | — | 159 ± 36 (9) | 156 ± 43 (8) |
|  |  | p = >0.05 | p = >0.05 |

TEST PROCEDURE II

Albino male rats are arranged in three groups (nine rats/group) and injected i.p. with nembutal at 50 mg/kg. Fifteen minutes after the nembutal injection they are injected s.c. according to group with (a) test compound, typically 500–2000 μg/kg; (b) SRIF 200 μg/kg; or (c) physiological saline. Ten minutes later 0.5 ml. of arginine (300 mg/ml, pH 7.2) is injected into the heart. The rats are decapitated five minutes after receiving the arginine, and the blood is collected into Trasylol-EDTA. Appropriate aliquots are then assayed for growth hormone, glucagon and insulin. An active compound is one which significantly changes the plasma level of any of these hormones from that of the saline controls. Comparisons between control and experimental values are statistically evaluated by the analysis of variants method and statistical significance (p) at 0.05 or lower is used as the index of activity.

| Compound (Dose) | GH (ng/ml) | Insulin (μ units/ml) | Glucagon (pg/ml) |
|---|---|---|---|
| A (3.35 mg/kg) | 31 ± 6 | 157 ± 8 | 3.0 ± 0.7 |
| Control | 149 ± 23 | 181 ± 6 | 6.4 ± 1.3 |
|  | p = <0.01 | p = <0.05 | p = <0.05 |
| A (1 mg/kg) | 38 ± 11 | 127 ± 10 | 57 ± 13 |
| Control | 191 ± 38 | 141 ± 6 | 96 ± 15 |
|  | p = <0.01 | p = >0.05 | p = ≦0.05 |
| A (0.2 mg/kg) | 57 ± 12 | 152 ± 15 | 32 ± 5 |
| SRIF (0.2 mg/kg) | 65 ± 16 | 111 ± 10 | 12 ± 3 |
| Control | 287 ± 53 | 151 ± 15 | 20 ± 1 |
|  | p = <0.01 | p = <0.05 | p = <0.05 |
| A (0.05 mg/kg) | 55  10 | — | — |
| SRIF (0.05 mg/kg) | 47  8 | — | — |
| Control | 170  49 | — | — |
|  | p = <0.05 |  |  |
| B (3.0 mg/kg.) | 92 ± 9 | 74 ± 13 | — |
| Control | 1009 ± 298 | 280 ± 37 | — |
|  | p = <0.01 | p = <0.01 |  |
| B (30 μg/kg.) | 180 ± 49 | — | — |
| SRIF (20 μg/kg.) | 232 ± 87 | — | — |
| Control | 619 ± 103 | — | — |
|  | p = <0.01 |  |  |
| B (2 μg/kg.) | 211 ± 18 | — | — |
| SRIF (10 μg/kg.) | 241 ± 15 | — | — |
| Control | 543 ± 86 | — | — |
|  | p = <0.01 |  |  |
| B (200 μg/kg.) | — | 66 ± 6 | 21 ± 5 |
| SRIF (200 μg/kg.) | — | 117 ± 12 | 13 ± 4 |
| Control | — | 167 ± 12 | 62 ± 8 |
|  |  | p = <0.01 | p = <0.01 |

The above test results demonstrate that the cyclic undecapeptides of this invention are useful in depressing the secretion of somatotropin, insulin, and glucagon in domestic animals and for the control of the immunoreactive pituitary growth hormone in comparative and experimental pharmacology. From the known relationship between growth hormone control in standard experimental animals and the human, the demonstrated pharmacological activity of the disclosed cyclic undecapeptides characterizes the compounds as useful in the treatment of acromegaly and juvenile diabetes in the same manner as somatostatin itself. Administration of the cyclic undecapeptides may be by conventional routes common to somatostatin and related polypeptides, under the guidance of a physician in an amount dictated by the extent of the dysfunction as determined by the physician. The compounds may be administered alone or in conjunction with conventional pharmaceutically acceptable carriers and adjuvants, in unit dosage form.

The following examples further illustrate the best mode contemplated by the inventor for the practice of the invention.

EXAMPLE 1 t-Butyloxycarbonyl-N$^\epsilon$-(2-Chlorobenzyloxycarbonyl)-L-Lysyl-L-Asparaginyl-L-Phenylalanyl-L-Phenylalanyl-L-Tryptophyl-N$^\epsilon$-(2-Chlorobenzyloxycarbonyl)-L-Lysyl-O-Benzyl-L-Threonyl-L-Phenylalanyl-O-Benzyl-L-Threonyl-O-Benzyl-L-Serine Resin, I and t-Butyloxycarbonyl-L-Phenylalanyl-O-Benzyl-L-Threonyl-O-Benzyl-L-Serine Resin, II. II is obtained as an intermediate in the preparation of I.

Chloromethylated polystyrene resin (400 g.) was esterified with the cesium salt of t-Boc-O-benzyl-serine (450 mmoles) by the method of B. F. Gisin, Helv. Chem. Acta, 56, 1476 (1973), to give t-Boc-O-benzyl-serine resin having a substitution of 0.63 mmoles/g. resin. The resin (470 g.) was then treated in the following manner:

1. Methanol wash (2 ×).
2. Methylene chloride wash (3 ×).
3. 5 min. prewash with 30% trifluoroacetic acid-methylene chloride (v/v) containing 5% ethanedithiol.
4. 30% trifluoroacetic acid-methylene chloride (v/v) containing 5% ethanedithiol (2 ×) for 15 mins. each.
5. Methylene chloride wash (2 ×).
6. Dimethylformamide wash.
7. 15% triethylamine in dimethylformamide (2 ×) for 10 min. each.
8. Dimethylformamide wash.
9. Methylene chloride wash.
10. Methanol wash (2 ×).
11. Methylene chloride wash (2 ×).

A contact time of 5 mins. was allowed for each wash unless otherwise indicated.

The resin was gently stirred with t-Boc-O-benzyl-L-threonine (146 g., 0.48 moles) in 1:1 dimethylformamide-methylene chloride solution and 1 molar dicyclohexylcarbodiimide (DCC) in methylene chloride (470 ml.) overnight. The resin was washed successively with dimethylformamide (twice), methanol (twice) and methylene chloride (twice). To test for completeness of reaction, the peptide resin was subjected to a ninhydrin in color test following the procedure of E. Kaiser, et al., Analytical Chemistry, 34, 595 (1970), and found to be weakly positive. The coupling step was repeated using t-Boc-O-benzyl-L-threonine (43.8 g., 0.14 moles in 1:1 dimethylformamide-methylene chloride, 70 ml. 1 molar DCC). After stirring overnight and the washing sequence described above, the reaction with ninhydrin was still slightly positive, so a further coupling with t-Boc-O-benzyl-L-threonine (43.8 g., 0.14 moles in dimethylformamide containing 1-hydroxybenzotriazole 21.9 g., 0.14 moles, 143 ml. 1 molar DCC) was performed. After stirring overnight and the washing sequence, the ninhydrin reaction was negative indicating complete coupling. Removal of the t-Boc-$\alpha$-amino protecting group was carried out as described in steps (3) through (11) above.

The following amino acid residues were then introduced consecutively. (A coupling time of 18 hr. was used for each amino acid unless specified otherwise. Each coupling between consecutive amino acids were separated by both the washing schedule and the deblocking sequence (3) through (11) described for the t-Boc-O-benzylserine resin). t-Boc-L-phenylalanine (187 g., 0.7 mmoles in dimethylformamide containing 1-hydroxybenzotriazole 107.9 g., 0.705 moles, 705 ml. 1 molar DCC). A 48.4 g. portion of peptide resin was removed and the synthesis continued with the addition of t-Boc-O-benzyl-L-threonine (145.3 g., 0.47 moles in dimethylformamide containing 1-hydroxybenzotriazole 71.9 g., 0.47 moles, 470 ml. 1 molar DCC), t-Boc-N$^\epsilon$-(2-chlorobenzyloxycarbonyl)-L-lysine (194.8 g., 0.47 moles in dimethylformamide containing 1-hydroxybenzotriazole 35 g., 0.23 moles, 470 ml. 1 molar DCC), t-Boc-L-tryptophan (142.9 g., 0.47 moles in dimethylformamide, 470 ml., 1 molar DCC). Incomplete coupling occurred at this stage, so after the washing sequence coupling with t-Boc-L-tryptophan was repeated using amino acid (72 g., 0.237 moles) in dimethylformamide containing 1-hydroxybenzotriazole (36 g., 0.237 moles) 235 ml. 1 molar DCC, 40 g. of peptide resin was removed and the synthesis continued with t-Boc-phenylalanine (124.6 g., 0.46 moles in dimethylformamide containing 1-hydroxybenzotriazole 71.9 g., 0.47 moles, 470 ml. 1 molar DCC). 43.3 g. of peptide resin was removed and the synthesis continued with the addition of t-Boc-L-asparagine-p-nitrophenyl ester (199.1 g., 0.56 moles in dimethylformamide containing 1% glacial acetic acid). A reaction time of 4 days was allowed for this stage. 52.4 g. of peptide resin was removed and the synthesis concluded with the addition of t-Boc-N$^\epsilon$-(2-chlorobenzyloxycarbonyl)-L-lysine (165.8 g., 0.4 moles in dimethylformamide containing 1-hydroxybenzotriazole 61.2 g., 0.4 moles, 400 ml. 1 molar DCC). The dried and washed resin weighed 568.1 g.

EXAMPLE 2

7-t-Butyloxycarbonylaminoheptanoic Acid

7-Aminoheptanoic acid (20 g., $1.38 \times 10^{-1}$ moles) was converted to the title compound using the method of Ulf Ragnarrson et al., Org. Syn., 53, 25 (1973), using tetramethylguanidine (17.3 g., $1.49 \times 10^{-1}$ moles) and t-butylphenylcarbonate (30 g., $1.54 \times 10^{-1}$ moles) in dimethylsulfoxide (100 ml.) for three days.

The product (24 g.) had m.p. 56-58° after recrystallization from ethyl acetate-hexane-ether.

Analysis for: $C_{12}H_{23}NO_4$.
Calculated: C, 58.75; H, 9.45; N, 5.71.
Found: C, 59.14; H, 9.61; N, 5.86.

EXAMPLE 3

7-t-Butyloxycarbonylaminoheptanoyl-N$^\epsilon$-(2-Chlorobenzyloxycarbonyl)-L-Lysyl-L-Asparaginyl-L-Phenylalanyl-L-Phenylalanyl-L-Tryptophyl-N$^\epsilon$-(2-Chlorobenzyloxycarbonyl)-L-Lysyl-O-Benzyl-L-Threonyl-L-Phenylalanyl-O-Benzyl-L-Threonyl-O-Benzyl-L-Serine Resin The peptide resin I (15 g.) from Example 1 was treated according to schedule (3) through (11) of Example 1 and the deblocked peptide resin stirred with 7-t-butyloxycarbonylaminoheptanoic acid (30 mmoles in 1:1 dimethylformamide-methylene chloride) and 60 ml. of an 0.5 molar solution of diisopropyl carbodiimide (DIC), in methylene chloride.

The peptide resin was washed with methylene chloride (twice), dimethylformamide (thrice) and methylene chloride (twice) to give the title resin.

EXAMPLE 4

7-t-Butyloxycarbonyl-N$^\epsilon$-(2-Chlorobenzyloxycarbonyl)-L-Lysyl-L-Asparaginyl-L-Phenylalanyl-L-Phenylalanyl-D-Tryptophyl-N$^\epsilon$-(2-Chlorobenzyloxycarbonyl)-L-Lysyl-O-Benzyl-L-Threonyl-L-Phenylylanyl-O-Benzyl-L-Threonyl-O-Benzyl-L-Serine Resin The peptide resin II from Example 1, t-Boc-L-phenylalanyl-O-benzyl-L-threonyl-O-benzyl-serine resin (10 g.), was converted into the title compound by the stepwise coupling of the appropriate amino acids in 1:1 methylene chloride-dimethyl-formamide (50 ml.) with an 0.5 molar solution (45 ml.) of dicyclohexylcarbodiimide (30 ml.). A coupling time of 18 hours was used for each amino acid. Each coupling was preceeded by the deblocking schedule and followed by the washing schedule as described.

DEBLOCKING SCHEDULE

1. Methylene chloride wash (3 ×).
2. Prewash with 40% trifluoroacetic acid in methylene chloride containing 0.5% w/v of dithioerythreitol.
3. Wash with 40% trifluoroacetic in methylene chloride containing 0.5% w/v of dithioerythreitol (2 ×) for 15 minutes each.
4. Wash with methylene chloride (2 ×).
5. Dimethylformamide wash (2 ×).
6. 15% triethylamine in dimethylformamide (2 ×) for 10 minutes each.
7. Dimethylformamide wash (2 ×).
8. Methylene chloride wash (3 ×).
9. Dimethylformamide wash.
10. Methylene chloride.

A contact time of 5 min. was allowed for each wash period.

Washing Schedule (i) Methylene chloride (2 ×).
(ii) Dimethylformamide (3 ×).
(iii) Methylene chloride (2 ×).

Amino acids in order of addition (20 mmoles).
t-Boc-O-benzyl-L-threonine (6.18 g.)
t-Boc-N$^\epsilon$-(2-chlorobenzyloxycarbonyl)-L-lysine (8.34 g.).
t-Boc-D-tryptophan (6.1 g.).
t-Boc-L-phenylalanine (5.3 g.).
t-Boc-L-phenylalanine (5.3 g.).
t-Boc-L-asparagine α-p-nitrophenyl ester (7.1 g.), no DIC was used with this coupling which was run in dimethylformamide containing 1% acetic acid.
t-Boc-N$^\epsilon$-(2-chlorobenzyloxycarbonyl)-L-lysine (8.34 g.).
7-t-Boc-aminoheptanoic acid (4.9 g.).

EXAMPLE 5

7-t-Butyloxycarbonylaminoheptanoyl-N$^\epsilon$-(2-Chlorobenzyloxycarbonyl)-L-lysyl-L-Asparaginyl-L-Phenylalanyl-L-Phenylalanyl-L-Tryptophyl-N$^\epsilon$-(2-Chlorobenzyloxycarbonyl)-L-Lysyl-O-Benzyl-L-Threonyl-L-Phenylalanyl-O-Benzyl-L-Threonyl-O-Benzyl-L-Seryl Hydrazide The peptide resin (15 g.) of Example 3 suspended in dry dimethylformamide (100 ml.) was stirred with 97% hydrazine (10 ml.) for 2 days at ambient temperatures under nitrogen. The resin was filtered and washed thoroughly with dimethylformamide. The combined filtrate and washings were concentrated under reduced pressure at temperatures not exceeding 30°. The residue was triturated with methanol (100 ml.) and filtered. The solid precipitate was stirred with methanol during 1 hour and agin filtered. The precipitate dried in vacuo over phosphorous pentoxide afforded 5.8 g. hydrazide.

EXAMPLE 6

7-t-Butyloxycarbonylaminoheptanoyl-N$^\epsilon$-(2-Chlorobenzyloxycarbonyl)-L-Lysyl-L-Asparaginyl-L-Phenylalanyl-L-Phenylalanyl-D-Tryptophyl-N$^\epsilon$-(2-Chlorobenzyloxycarbonyl)-L-Lysyl-O-Benzyl-L-Threonyl-L-Phenyl-alanyl-O-Benzyl-L-Threonyl-O-Benzyl-L-Seryl Hydrazide The total peptide resin of Example 4 was washed with dimethylformamide and then suspended in dry dimethylformamide (100 ml.) and stirred with 97% hydrazine (10 ml.) for two days at room temperature under nitrogen. The resin was filtered and washed thoroughly with dimethylformamide. The combined filtrate and washings were concentrated under reduced pressure at temperatures not exceeding 30°. The residue was triturated with methanol and filtered. The solid precipitate was stirred with methanol during 1 hour and again filtered. The precipitate dried in vacuo after phosphorous pentoxide afforded 4.9 g. crude hydrazide.

EXAMPLE 7

Cyclic(7-Aminoheptanoyl-N$^\epsilon$-(2-Chlorobenzyloxycarbonyl)-L-Lysyl-L-Asparaginyl-L-Phenylalanyl-L-Phenylalanyl-L-Tryptophyl-N$^\epsilon$-(2-Chlorobenzyloxycarbonyl)-L-Lysyl-O-Benzyl-L-Threonyl-L-Phenylalanyl-O-Benzyl-L-Threonyl-O-Benzyl-L-Seryl)

The crude dried hydrazide of Example 5 suspended in anhydrous trifluoroacetic acid (60 ml.), methylene chloride (40 ml.), anisole (5 ml.) was stirred with 0.5 g. dithioerythreitol during 15 minutes at 0° and then for a further 45 mins. at room temperature. The clear solution was evaporated to an oil which, on trituration with large volumes of ether afforded a flocculent solid (5.65 g.), which was dried in vacuo over phosphorous pentoxide.

The above solid (5.5 g., 2.4 mmoles) dissolved in dimethylformamide (60 ml.) at room temperature was cooled to −30° and treated with 12.2 ml. of 0.76N hydrogen chloride (9.27 moles) in tetrahydrofuran followed by t-butylnitrite (0.36 ml., 3.1 mmoles). The solution had a negative reaction with ammoniacal silver nitrate (Tollen's reagent) after 30 min. in the −20°-−30° temperature range indicating absence of hydrazide. The reaction mixture was transferred to a flask containing anhydrous dimethylformamide (2L) at −20° and the pH adjusted to 8 with diisopropylethylamine. The reaction mixture was stored at 0°, during 3 days and then evaporated to a small volume under reduced pressure. The residue was poured into 500 ml. 1% acetic acid stood overnight at 0° and filtered. The solid was washed with water and dried in vacuo to give the title product (4.7 g.).

EXAMPLE 8

Cyclic(7-Aminoheptanoyl-N$^\epsilon$-(2-Chlorobenzyloxycarbonyl)-L-Lysyl-L-Asparaginyl-L-Phenylalanyl-L-Phenylalanyl-D-Tryptophyl-N$^\epsilon$-(2-Chlorobenzyloxycarbonyl)-L-Lysyl-O-Benzyl-L-Threonyl-L-Phenylalanyl-O-Benzyl-L-Threonyl-O-Benzyl-L-Seryl)

The crude hydrazide of Example 6 (4.9 g.) was stirred in a mixture of anhydrous trifluoroacetic acid (100 ml.), and anisole (5 ml.) containing dithioerythreitol (0.5 g.) during 10 mins. at 0° and then for a further 50 mins. at room temperature. The clear solution was evaporated to an oil which on trituration with large volumes of ether afforded a solid (4.8 g.) after drying in vacuo over phosphorous pentoxide.

The above solid (4.8 g., 2.1 mmoles) dissolved in dimethylformamide (50 ml.) at room temperature was cooled to −30° and treated with 2 ml. 4N hydrogen chloride (8 mmoles) in dioxane followed by t-butylnitrite (0.31 ml., 2.68 mmoles). The solution had a negative reaction with ammoniacal silver nitrate (Tollen's reagent) after 30 minutes in the −20° to −30° temperature range indicating absence of hydrazide. The reaction mixture was transferred to a flask containing anhydrous dimethylformamide (2L) at −20° and the pH adjusted to 8 with diisopropylethylamine. The reaction mixture was stored at 0° during 4½ days and then evaporated in vacuo at temperatures <35°. The residue was poured into 500 ml. 1% acetic acid and the solid recovered by filtration. After washing with water and drying in vacuo over phosphorous pentoxide, 4.2 g. product was obtained.

EXAMPLE 9

Cyclic(7-Aminoheptanoyl-L-Lysyl-L-Asparaginyl-L-Phenylalanyl-L-Phenylalanyl-L-Tryptophyl-L-Lysyl-L-Threonyl-L-Phenylalanyl-L-Threonyl-L-Seryl)

Cyclic(7-aminopentanoyl-N$^\epsilon$-(2-chlorobenzyloxycarbonyl)-L-lysyl-L-asparaginyl-L-phenylalanyl-L-phenylalanyl-L-tryptophyl-N$^\epsilon$-(2-chlorobenzyloxycarbonyl)-L-lysyl-O-benzyl-L-threonyl-L-phenyl-alanyl-O-benzyl-L-threonyl-O-benzyl-L-seryl) (4.6 g.) was treated in vacuo with anhydrous hydrogen fluoride (100 ml.) and anisole (30 ml.) at 0° during 1 hour. Hydrogen fluoride was removed under reduced pressure and the residue triturated thoroughly with ether prior to extraction with degassed 20% acetic acid (100 ml.). The acid fraction was diluted with water and lyophyllized to leave the crude title compound (3.15 g.).

Purification

The crude deprotected peptide (3.1 g.) in 20% acetic acid was applied to a column of Sephadex G 25 (fine), 200 × 2.5 cm. in 20% acetic acid. 180 fractions (5.6 ml. each) were collected. Column effluent was monitored at 254 mµ with an Altex Model 153 Analytical UV Detector using an Altex preparative Flow Cell and omniscribe recorder. Four major fractions were taken A (82–94) 267 mg.; B (99–107) 883 mg.; C (111–119) 970 mg.; D (120–136) 700 mg. Fraction D (120–136) was selected for further purification on the basis of tlc, amino acid analysis, and positive tryptophan reaction with Ehrlich reagent. Resizing on the same column afforded a single peak in fractions 116–127 (5.6 ml. each) 491 mg. (70% recovery). Further purification was effected on a partition column (150 × 2.5 cm.) of Sephadex G-25 fine prepared by equilibration with lower phase and then upper phase of the solvent system: n-butanol:acetic acid:water 4:1:5. Column effluent monitored as above afforded homogeneous material in fractions 48–61. The fractions were collected, evaporated and lyophyllized from 10% acetic acid. The solid was dissolved in 1% acetic acid filtered through an 0.3 μm Millipore ® filter and lyophyllized to give 250 mg. product. $[\alpha]_D^{26}$ −27.5 c., 1.18 1% acetic acid.

Amino acid analysis for a sample hydrolyzed 18 hr. at 110° in an evacuated sealed tube containing 4N methane sulfonic acid and 0.2% 3-(2-aminoethyl) indole.

Asp (1.0), Thr (1.88), Ser (0.94), Phe (2.97), 7-$NH_2(CH_2)_6\text{-}CO_2H$ (1.0), Lys (2.03), $NH_3$ (0.79), Trp (0.95).

No loss of 7-aminoheptanoic acid was observed relative to phenylalanine after exhaustive free amine dansylation and subsequent amino acid hydrolysis under conditions causing complete loss of lysine.

Thin Layer Chromatography

| $R_f$ values | I | II | III |
|---|---|---|---|
| Silica gel | 0.3 | 0.77 | 0.54 |
| Cellulose | 0.6 | 0.88 | 0.60 |

$R_f$ values determined on 5 × 20 cm. Brinkmann $SiO_2$ gel 60 F-254 and on a 5 × 20 cm. Avicel Analtech plates. The spots were visualized by iodine and Ehrlich reagent.

Solvent System.

I Butanol:acetic acid:water (4:1:5).
II Ethyl acetate:butanol:acetic acid:water (1:1:1:1).
III Isoamyl alcohol:pyridine:water (7:7:6).

EXAMPLE 10

Cyclic(7-Aminoheptanoyl-L-Lysyl-L-Asparaginyl-L-Phenylalanyl-L-Phenylalanyl-D-Tryptophyl-L-Lysyl-L-Threonyl-L-Phenylalanyl-L-Threonyl-L-Seryl)

Cyclic(7-aminoheptanoyl-$N^\epsilon$-(2-chlorobenzyloxycarbonyl)-L-lysyl-L-asparaginyl-L-phenylalanyl-L-phenylalanyl-D-tryptophyl-$N^\epsilon$-(2-chlorobenzyloxycarbonyl)-L-lysyl-O-benzyl-L-threonyl-L-phenylalanyl-O-benzyl-L-threonyl-O-benzyl-L-seryl) (4.3 g.) was treated in vacuo with anhydrous hydrogen fluoride (100 ml.) and anisole (30 ml.) at 0° during 1 hour. Hydrogen fluoride was removed under reduced pressure and the residue triturated thoroughly with ether prior to extraction with degassed 20% acetic acid (100 ml.). The acid fraction was diluted with water and lyophyllized to leave the title compound (2.55 g.).

Purification

The crude deprotected peptide (2.50 g.) in 20% acetic acid was applied to a column of Sephadex G-25 (fine), 200 × 2.5 cm. in 20% acetic acid. 180 fractions (5.6 ml. each) were collected. Column effluent was monitored as described for Example 9. Tryptophan positive fractions were collected lyophyllized to give 1.0 g. peptide which was reapplied to the column. Fractions 129–148 (295 mg.) were selected, on the basis of tlc and amino acid analysis, for further purification. Fractions 129–148 were reapplied to a partition column (150 × 2.5 cm.) of Sephadex G-25 fine prepared by equilibration with lower phase and then upper phase of the solvent system: n-butanol:acetic acid:water — 4:1:5. Column effluent monitored as above afforded homogeneous material in fractions 74–94. The fractions were collected, evaporated and the residue lyophyllized from 10% acetic acid. The solid was dissolved in 1% acetic acid filtered through an 0.3 μm Millipore ® filter and lyophyllized to give 120 mg. product. $[\alpha]_D^{26}$ −31.5° c., 1.11% acetic acid.

Amino acid analysis for a sample hydrolyzed 18 hours at 110° in an evacuated sealed tube containing 4N methane sulfonic acid and 0.2% 3-(2-aminoethyl)indole.

Asp (1.0), Thr (1.83), Ser (1.05), Phe (2.88), $NH_2(CH_2)_6CO_2H$ (1.0), Lys (1.99), $NH_3$ (1.03), Trp (0.87).

No loss of 7-aminoheptanoic acid was observed relative to phenylalanine after exhaustive free amine dansylation and subsequent amino acid hydrolysis under conditions causing complete loss of lysine.

Thin Layer Chromatography

| $R_f$ Values | I | II | III |
|---|---|---|---|
| Silica gel | 0.32 | 0.77 | 0.54 |
| Cellulose | 0.60 | 0.88 | 0.64 |

Origin of plates and meaning of solvent systems I, II, and III as in Example 9.

The subject matter which the applicant regards as his invention is particularly pointed out and distinctly claimed as follows:

1. A compound selected from the class consisting of

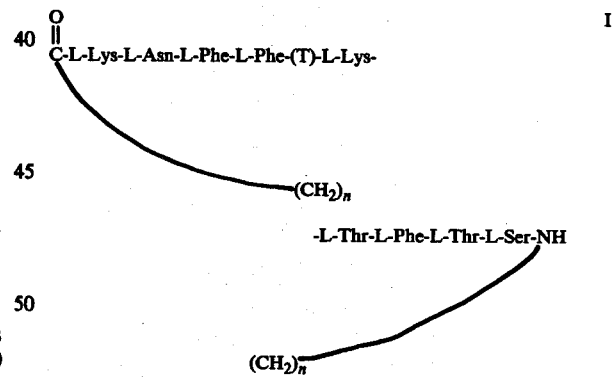

and

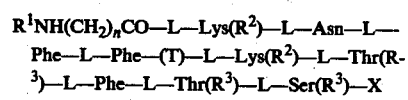

$$R^1NH(CH_2)_nCO\text{—}L\text{—}Lys(R^2)\text{—}L\text{—}Asn\text{—}L\text{—}$$
$$Phe\text{—}L\text{—}Phe\text{—}(T)\text{—}L\text{—}Lys(R^2)\text{—}L\text{—}Thr(R^3)\text{—}L\text{—}Phe\text{—}L\text{—}Thr(R^3)\text{—}L\text{—}Ser(R^3)\text{—}X$$

and its non-toxic salts wherein $R^1$ is selected from the group consisting of hydrogen and t-butyloxycarbonyl; $R^2$ is 2-chlorobenzyloxycarbonyl; $R^3$ is benzyl; n is an integer of from 3 to 8; T is selected from the group consisting of L-Tryptophyl and D-Tryptophyl; and X is selected from the group consisting of OH, NH—$NH_2$, O-(lower)alkyl, O-benzyl and an anchoring bond linked to a solid polystyrene resin represented by:

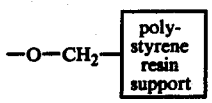

2. A compound according to formula II of claim 1 wherein X is NH—NH$_2$.

3. A compound according to claim 1 wherein T is L-tryptophyl and n is 6.

4. A compound according to claim 1 wherein T is D-tryptophyl and n is 6.

5. A compound according to claim 1 which is selected from:

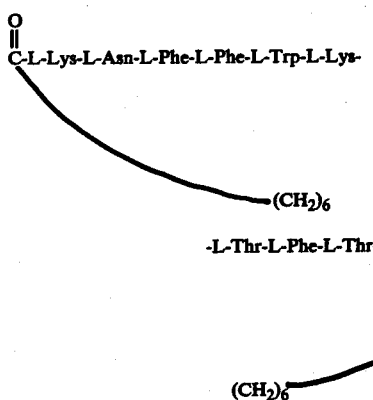

and its non-toxic acid addition salts.

6. A compound according to claim 1 which is selected from:

[structure showing:
O
‖
C-L-Lys-L-Asn-L-Phe-L-Phe-L-D-Trp-L-
          (CH$_2$)$_6$
-Lys-L-Thr-L-Phe-L-Thr-L-Ser-NH
          (CH$_2$)$_6$]

and its non-toxic acid addition salts.

7. A compound of the formula:

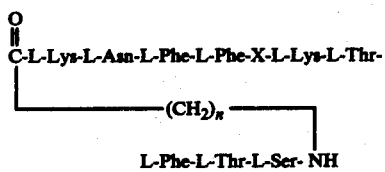

wherein n = 4–6 and X is L-Trp or D-Trp.

* * * * *